(12) United States Patent
He

(10) Patent No.: US 10,816,542 B2
(45) Date of Patent: Oct. 27, 2020

(54) TEAR GLUCOSE MEASURING DEVICE

(71) Applicant: SHANGHAI WEIYIN BIOTECHNOLOGY CO., LTD., Shanghai (CN)

(72) Inventor: Jianhui He, Shanghai (CN)

(73) Assignee: SHANGHAI WEIYIN BIOTECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 15/750,930

(22) PCT Filed: Jan. 13, 2016

(86) PCT No.: PCT/CN2016/070801
§ 371 (c)(1),
(2) Date: Feb. 7, 2018

(87) PCT Pub. No.: WO2017/028486
PCT Pub. Date: Feb. 23, 2017

(65) Prior Publication Data
US 2018/0231529 A1    Aug. 16, 2018

(30) Foreign Application Priority Data

Aug. 18, 2015   (CN) .......................... 2015 1 0508889

(51) Int. Cl.
*G01N 33/52* (2006.01)
*G01N 21/77* (2006.01)
(Continued)

(52) U.S. Cl.
CPC ....... *G01N 33/525* (2013.01); *A61B 5/14507* (2013.01); *A61B 5/14532* (2013.01);
(Continued)

(58) Field of Classification Search
CPC ......... G01N 33/525; G01N 2021/7759; G01N 2021/7786; G01N 21/77; G01N 21/78;
(Continued)

(56) References Cited

U.S. PATENT DOCUMENTS 5,413,761 A  *  5/1995  Dulaney .............. G01N 33/521
                                                                422/401
2002/0146835 A1    10/2002  Modzelewski et al.
(Continued)

FOREIGN PATENT DOCUMENTS

CN              2625897 Y       7/2004
CN           104094114 A       10/2014
(Continued)

OTHER PUBLICATIONS

English translation of CN 2625897 (Year: 2019).*
English translation of CN104215758 (Year: 2019).*

*Primary Examiner* — William H. Beisner
*Assistant Examiner* — Danielle B Henkel
(74) *Attorney, Agent, or Firm* — Muncy, Geissler, Olds & Lowe, P.C.

(57) ABSTRACT

A tear glucose measuring device includes a tear glucose test strip (101) and a reaction device, wherein the tear glucose test strip (101) is used for collecting tears which are then subjected to an elution reaction with a glucose assay reagent contained in the reaction device. With this device, a user can collect tears by himself by folding a leading portion (1014) of the tear glucose test strip (101) about a folding line (1021) and inserting the leading portion (1014) into the lower conjunctival sac inside the lower eyelid to allow the absorbance of tears therein. If tear glucose test strips (101) of the same lot are consistent in terms of thickness of a moisture-absorbent layer of the leading portion (1014), as long as a tear collection region (1020) of the leading portion (1014) has a fixed area, the leading portion (1014) can collect a (Continued)

quantitative amount of tears. As such, tears can be sampled without needing to stimulate the lacrimal gland, and glucose in the collected tears will not be diluted and thus reflect the patient's true tear glucose level.

12 Claims, 5 Drawing Sheets

(51) Int. Cl.
    *A61B 5/145*     (2006.01)
    *G01N 33/66*     (2006.01)
    *G01N 21/78*     (2006.01)
    *A61B 10/00*     (2006.01)

(52) U.S. Cl.
    CPC ......... *A61B 10/0045* (2013.01); *G01N 21/77* (2013.01); *G01N 21/78* (2013.01); *G01N 33/526* (2013.01); *G01N 33/66* (2013.01); *A61B 2010/0006* (2013.01); *A61B 2010/0067* (2013.01); *G01N 2021/7759* (2013.01); *G01N 2021/7786* (2013.01)

(58) Field of Classification Search
    CPC .. G01N 33/526; G01N 33/66; A61B 5/14507; A61B 5/14532; A61B 10/0045; A61B 2010/0006; A61B 2010/0067
    See application file for complete search history.

(56) References Cited

U.S. PATENT DOCUMENTS

| | | | | |
|---|---|---|---|---|
| 2003/0185708 | A1* | 10/2003 | Otake | G01N 33/48757 422/404 |
| 2003/0190259 | A1* | 10/2003 | Alley | A61B 10/0096 422/411 |
| 2003/0211625 | A1 | 11/2003 | Cha et al. | |
| 2004/0076547 | A1* | 4/2004 | Carney | A61B 10/0045 422/82.08 |
| 2009/0298191 | A1* | 12/2009 | Whitesides | G01N 33/523 436/164 |
| 2014/0262830 | A1 | 9/2014 | Cha et al. | |
| 2015/0244852 | A1* | 8/2015 | Erickson | G01N 21/31 455/557 |

FOREIGN PATENT DOCUMENTS

| | | |
|---|---|---|
| CN | 203898277 U | 10/2014 |
| CN | 104215758 A | 12/2014 |
| CN | 105044070 A | 11/2015 |
| CN | 204924945 U | 12/2015 |

\* cited by examiner

TEAR GLUCOSE MEASURING DEVICE

TECHNICAL FIELD

The present invention relates to the field of biotechnology and, in particular, to a device for detecting glucose in tears.

BACKGROUND

Diabetes mellitus (DM) is a chronic metabolic disease characterized by a high blood sugar level due to the accumulation of excessive glucose in the blood mainly as a result of insufficient secretion of insulin by pancreatic β-cells or malfunction of the secreted insulin, i.e., failure in transporting the absorbed glucose into cells for its conversion to life-supporting energy and in effective storage of the glucose. As DM is incurable and the high blood sugar level may have serious consequences if prolonged, it is necessary to monitor the blood sugar level and maintain it within the normal range. By 2010, there will be 280 million diabetic patients all over the world and the prevalence of diabetes in 20- to 79-year-old population group will reach 6.6%, in which 70% will come from low- and middle-income countries. In 2010, diabetic patients averagely pay 703 US dollars in relation to diabetes. IMS statistics show that the global sales of anti-diabetic drugs have exceeded 30 billion US dollars in 2009. According to a survey conducted by the National Health and Family Planning Commission of the P. R. C, there are currently at least 34 million diabetic patients in China, accounting for about 2.6% of China's total population. 30 years ago, this figure was only 0.7%. Additionally, the World Health Organization has projected that, by 2025, the number of diabetic patients will be 300 million worldwide and that China will top the world in terms of the number of diabetic patients. At present, the most common method used by diabetic patients for daily blood sugar level monitoring is to measure the concentration of glucose in the whole blood based on a trace sample collected from the fingertip by acupuncture under fasting conditions. However, this approach can cause patient pain and is associated with a risk of cross-contamination. Researchers are currently devoted to noninvasive blood glucose detection. In terms of glucose detection, except for blood, tears provide a source of human specimens that are less affected by external factors compared to saliva and urine. Medical studies have revealed that tears contain more than 20 substances including proteins, small molecules and minerals. The first report about the presence of glucose in tears was published in 1932, suggesting that the tear glucose level was maintained at a fixed ratio to the blood sugar level. In 2005, Dr. Chatterjee from the Eye Institute of Indiana, the United States conducted a study on 200 diabetic patients and found that their tear glucose levels reflected and varied with their blood sugar levels. It has been reported that, in a randomized study, Dr. P. R. Chatterjee and colleagues from the Regional Institute of Ophthalmology, Kolkata, India observed and analyzed the correlation between blood glucose levels and tear glucose levels in 200 individuals attending their clinic and quantitatively measured the blood glucose levels. Dr. Chatterjee stressed that 91.2% of the patients with varying grades of hyperglycemia recorded a positive color response for glucose in tears, which was highly consistent with the results of blood sugar tests. Correlation between blood sugar and tear glucose levels were also noted in the patients who were subjected to the glucose tolerance test.

At present, tear glucose samples are collected mainly by stimulation with cotton swabs or by using capillaries. However, both of these methods require operation by professionals rather than the patients themselves because they may impose a great risk. In addition, as these two methods are barely capable of quantitative collection and necessitate the use of high-precision liquid chromatography, they cannot be used for daily noninvasive self-monitoring of diabetic patients.

SUMMARY OF THE INVENTION

It is an objective of the present invention to solve the above-described problems by presenting a tear glucose measuring device which allows a user to perform quantitative collection of tears by himself without involving professional personnel.

To this end, a tear glucose measuring device according to the present invention includes: a tear glucose test strip and a reaction device, the tear glucose test strip is configured for collecting tears which are then subjected to an elution reaction with a glucose assay reagent contained in the reaction device, the tear glucose test strip has a strip shape and includes a leading portion and a holder portion, the leading portion and the holder portion have a folding line formed therebetween, the leading portion is foldable about the folding line.

Preferably, in the tear glucose measuring device, on each side of the folding line there is formed a V-notch.

Preferably, in the tear glucose measuring device, the leading portion may include: a tear collection region for collecting tears; and a barrier region for limiting an amount of tears collected by the tear collection region.

Preferably, in the tear glucose measuring device, the tear collection region may include a first portion of a moisture-absorbent layer, the barrier region may include a stack of a portion of a first hydrophobic layer, a second portion of the moisture-absorbent layer and a portion of a second hydrophobic layer, and the second portion of the moisture-absorbent layer is sandwiched between the portion of the first hydrophobic layer and the portion of the second hydrophobic layer.

Preferably, in the tear glucose measuring device, the holder portion may include a stack of another portion of the first hydrophobic layer, a third portion of the moisture-absorbent layer and another portion of the second hydrophobic layer, and the third portion of the moisture-absorbent layer is sandwiched between the another portion of the first hydrophobic layer and the another portion of the second hydrophobic layer.

Preferably, in the tear glucose measuring device, the tear collection region may include a first moisture-absorbent layer, a first portion of a hydrophobic layer and a second moisture-absorbent layer, the first portion of the hydrophobic layer is sandwiched between the first moisture-absorbent layer and the second moisture-absorbent layer, and the barrier region comprises a second portion of the hydrophobic layer.

Preferably, in the tear glucose measuring device, the holder portion may include a third portion of the hydrophobic layer.

Preferably, in the tear glucose measuring device, the leading portion may have a length of 4 mm to 6 mm.

Preferably, in the tear glucose measuring device, the holder portion may include a first holder portion and a second holder portion joined to each other, and wherein the first holder portion has a width smaller than a width of the second holder portion.

Preferably, in the tear glucose measuring device, the reaction device may be a cuvette including a holder section, a colorimetric section and a lid, the holder section is in communication with the colorimetric section, the lid is disposed on the top of the holder section and is configured to seal the holder section and the colorimetric section, the lid defines a slit through which the leading portion and first holder portion of the tear glucose test strip is insertable into the cuvette, the slit has a length that is smaller than the width of the second holder portion.

Preferably, in the tear glucose measuring device, each of the holder section and the colorimetric section may have a shape of a hollow column, and the holder section may have a size greater than a size of the colorimetric section.

Preferably, in the tear glucose measuring device, each of the holder section and the colorimetric section may have a shape of a hollow rectangular parallelepiped, and the slit extends diagonally in the lid.

Preferably, in the tear glucose measuring device, the reaction device is a horseshoe-shaped fluorescence plate defining a pocket, a first reservoir and a second reservoir, the first reservoir in communication with a bottom of the pocket via a first channel, the second reservoir in communication with the bottom of the pocket via a second channel, wherein the tear glucose test strip is insertable into the bottom of the pocket.

Preferably, in the tear glucose measuring device, the width of the second holder portion of the tear glucose test strip is greater than a width of the pocket.

With the tear glucose measuring device according to the present invention, a user can collect tears by himself by folding the leading portion of the tear glucose test strip about the folding line and inserting the leading portion into the lower conjunctival sac inside the lower eyelid to allow the absorbance of tears therein. As long as the tear collection region of the leading portion has a fixed area, the leading portion can collect a quantitative amount of tears. As such, tears can be sampled without needing to stimulate the lacrimal gland, and glucose in the collected tears will not be diluted and thus reflect the patient's true tear glucose level.

In these figures, 101-tear glucose test strip; 102-cuvette; 103-fluorescence plate;

1011-first hydrophobic layer; 1012-moisture-absorbent layer; 1013-second hydrophobic layer; 1014-leading portion; 1015-holder portion; 1016-second holder portion; 1017-shoulder portion; 1018-first holder portion; 1019-barrier region; 1020-tear collection region; 1021-folding line; 1022-V-notch;

2011-lid; 2012-holder section; 2013-colorimetric section; 2014-slit;

3011-pocket; 3012-first reservoir; 3013-first channel; 3014-second reservoir; 3015-second channel;

201-tear glucose test strip; 2201-first moisture-absorbent layer; 2202-second moisture-absorbent layer; and 2203-hydrophobic layer.

DETAILED DESCRIPTION

A few specific embodiments of the present invention will be described in greater detail below with reference to the accompany drawings. Features and advantages of the invention will be more apparent from the following detailed description, and from the appended claims. Note that the figures are provided in a very simplified form not necessarily presented to scale, with the only intention of facilitating convenience and clarity in explaining the embodiments.

Embodiment 1

Figure 1:
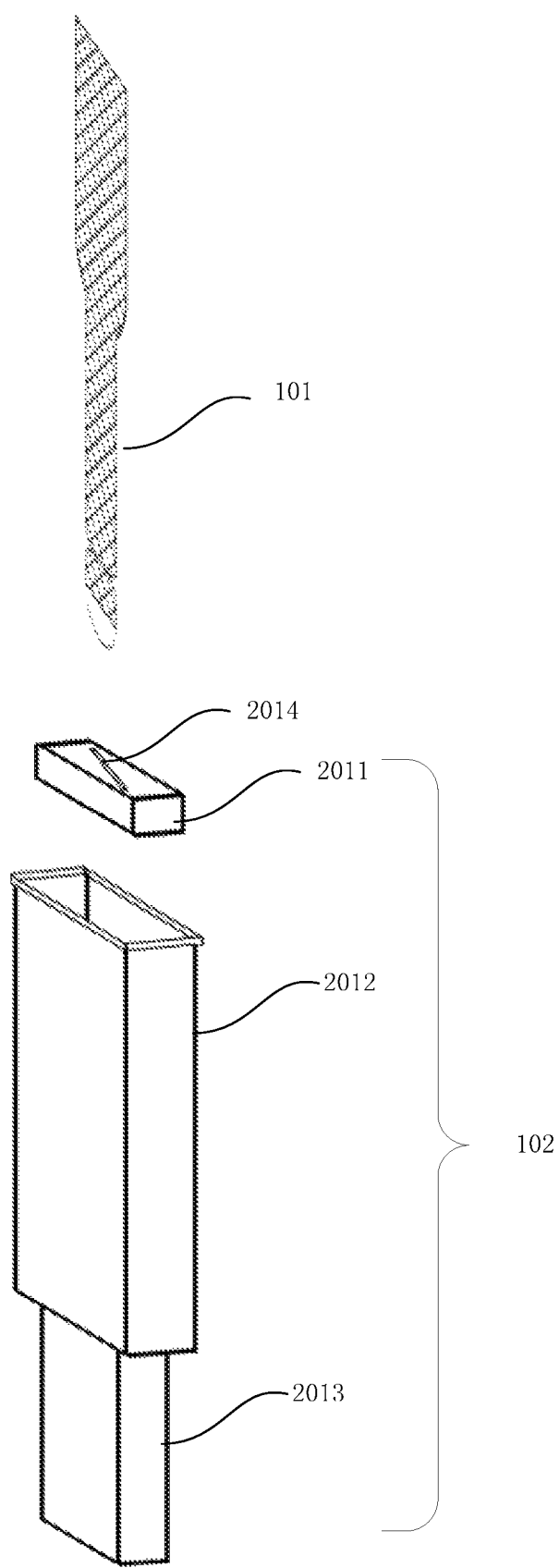
FIG. 1 is a structural schematic of a tear glucose measuring device according to a first embodiment of the present invention.
Figure 3:
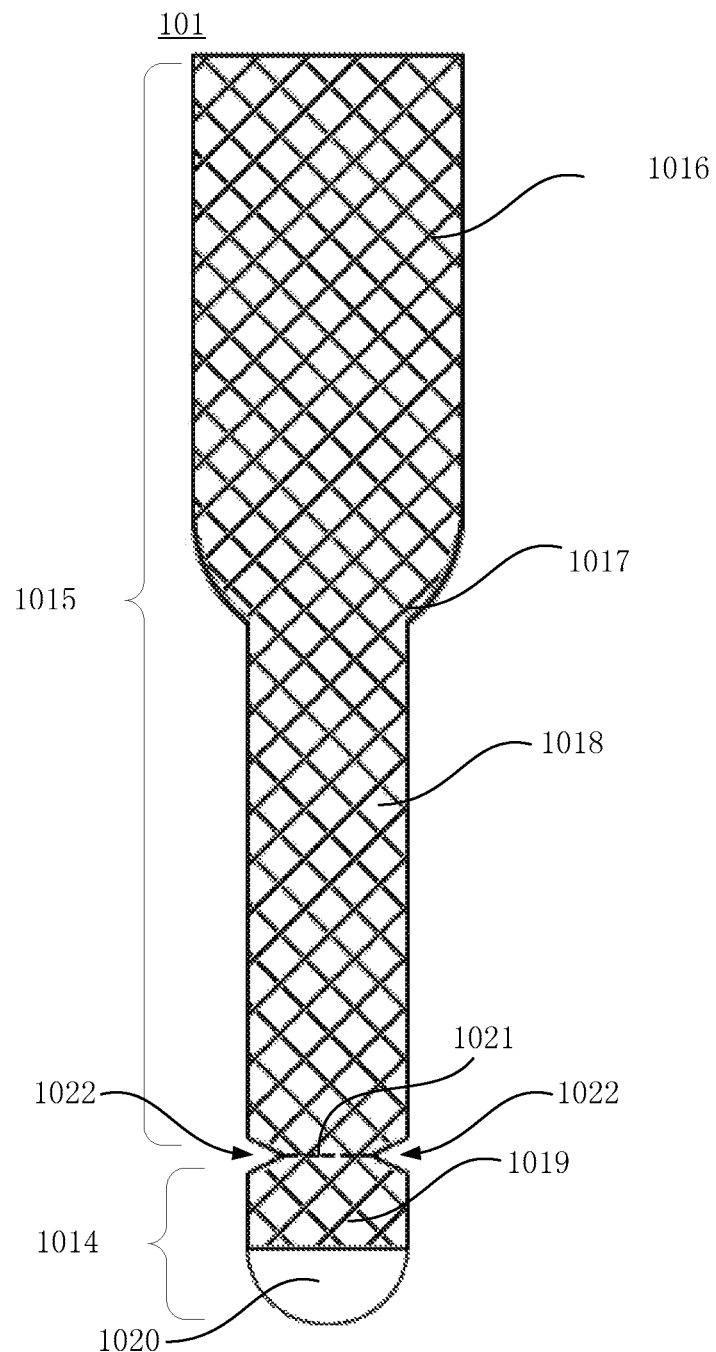
FIG. 3 is a structural schematic of the tear glucose test strip according to the first embodiment of the present invention.

As shown in FIGS. 1 and 3, in an embodiment of the present invention, there is provided a tear glucose measuring device which specifically includes a tear glucose test strip 101 and a reaction device which is a cuvette 102. The tear glucose test strip 101 has a strip shape and includes a leading portion 1014 and a holder portion 1015, there is provided a folding line 1021 between the leading portion 1014 and the holder portion 1015. The leading portion 1014 can be folded about the folding line 1021 by 90 degrees. The holder portion 1015 includes a first holder portion 1018 and a second holder portion 1016. The first holder portion 1018 has a width smaller than that of the second holder portion 1016. The cuvette 102 includes a holder section 2012 and a colorimetric section 2013, the holder section 2012 is in communication with the colorimetric section 2013. The holder section 2012 defines an opening on the top through which the leading portion 1014 and the first holder portion 1018 of the tear glucose test strip 101 are inserted into the cuvette 102. The size (width) of the opening is smaller than a width of the second holder portion 1016, greater than or equal to a maximum width of the leading portion 1014 and greater than or equal to a width of the first holder portion 1018. The colorimetric section 2013 of the cuvette 102 contains a glucose oxidase endpoint assay reagent in which the leading portion 1014 of the tear glucose test strip 101 is dipped in to enable an elution reaction to occur.

Figure 2:
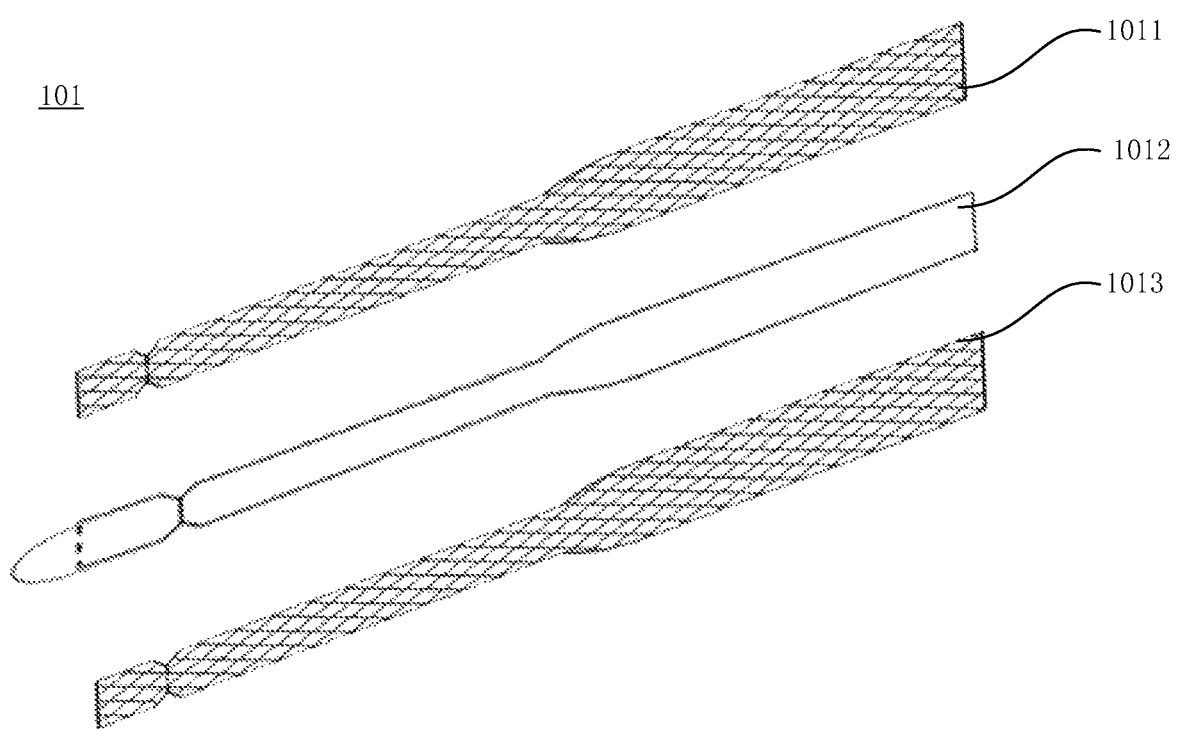
FIG. 2 is a structural schematic of layers of a tear glucose test strip according to the first embodiment of the present invention.

Specifically, as shown in FIG. 3, the leading portion 1014 of the tear glucose test strip 101 includes a tear collection region 1020 and a barrier region 1019. The tear collection region 1020 is configured to collect tears, and the barrier region 1019 is adapted to limit the volume of tears collected by the tear collection region 1020. Additionally, as shown in FIG. 2, the tear collection region 1020 consists of a portion of a moisture-absorbent layer 1012, while the barrier region 1019 is made up of a stack of a portion of a first hydrophobic layer 1011, another portion of the moisture-absorbent layer 1012 and a portion of a second hydrophobic layer 1013. The moisture-absorbent layer 1012 is sandwiched between the first hydrophobic layer 1011 and the second hydrophobic layer 1013. The portions of the moisture-absorbent layer 1012 respectively in the tear collection region 1020 and the barrier region 1019 are joined together and formed of the same hydrophilic material which is, for example, a cotton or wood fiber material. The first hydrophobic layer 1011 and the second hydrophobic layer 1013 are both a hydrophobic material such as, for example, an oily paint or plastic.

The tear collection region 1020 and the barrier region 1019 are demarcated by a boundary line. As the moisture-absorbent layer 1012 is covered by the first hydrophobic layer 1011 and the second hydrophobic layer 1013 in the barrier region 1019, tears collected in the tear collection region 1020 cannot cross over the boundary line into the barrier region 1019. As long as moisture-absorbent layers 1012 of the same lot are consistent in thickness, the area of the tear collection region 1020 can be determined by the amount of tears to be collected to enable quantitative collection. The end of the tear collection region 1020 distant from the barrier region 1019 is rounded so as to easily fit onto the lower eyelid.

The tear glucose test strip 101 has a length of 10-50 mm. The leading portion 1014 has a length of 4-6 mm. The end of the tear collection region 1020 distant from the barrier region 1019 has a radius of 1-5 mm. The tear collection region can collect 1-5 µL of tears. The first holder portion 1018 has a width of 2-10 mm, and the second holder portion 1016 has a width of 5-15 mm. The first holder portion 1018 has a width smaller than that of the second holder portion 1016.

Similar to the barrier region 1019, the holder portion 1015 of the tear glucose test strip 101 is made up of a stack of the remainders of the first hydrophobic layer 1011, the moisture-absorbent layer 1012 and the second hydrophobic layer 1013. The holder portion 1015 is joined to the barrier region 1019 by the folding line 1021, there is formed a V-notch 1022 on each side of the folding line 1021. The holder portion 1015 includes the first holder portion 1018 and the second holder portion 1016. The first holder portion 1018 and the second holder portion 1016 are joined together by a shoulder portion 1017, and the first holder portion 1018 has a width smaller than a width of the second holder portion 1016, the first holder portion 1018 has a width equal to a width of the barrier region 1019, and the barrier region 1019 has a width greater than or equal to a maximum width of the tear collection region 1020.

In other embodiments of the present invention, the holder portion 1015 and barrier region 1019 of the tear glucose test strip 101 may also be single-layered structures, as long as they can make the moisture-absorbent layer unable to absorb moisture. Further description in this regard is deemed to be unnecessary.

In addition to the holder section 2012 and the colorimetric section 2013, the cuvette 102 further includes a lid 2011. The holder section 2012 and the colorimetric section 2013 are in communication with each other and are both hollow columns. The holder section 2012 has a size greater than a size of the colorimetric section 2013, and the bottom of the holder section 2012 is in communication with the top of the colorimetric section 2013. The lid 2011 is disposed on the top of the holder section 2012 and is configured to seal the colorimetric section 2013 and the holder section 2012. The lid 2011 defines a slit 2014 extending therein. The slit 2014 is disposed in the lid diagonally. The slit 2014 has a length that is greater than or equal to the width of the first holder portion 1018 but smaller than the width of the second holder portion 1016. The first holder portion 1018 has a length that is smaller than or equal to a length of the holder section 2012. Preferably, the length of the first holder portion 1018 is substantially equal to that of the holder section 2012 so that only the leading portion 1014 can be inserted into the colorimetric section 2013.

The circumference of the lid 2011 is complementary in shape to a top portion of an inner wall of the holder section 2012. When the lid 2011 is deployed in place, it is flush with the top of the holder section 2012 so that contact edges of the lid 2011 and the holder section 2012 can be easily sealed by aluminum foil to prevent the reagent from escaping from the colorimetric section 2013 due to evaporation.

Preferably, in this embodiment, the holder section 2012 and the colorimetric section 2013 are both hollow rectangular parallelepipeds, and the slit 2014 extends diagonally in the lid 2011 to prevent the tear glucose test strip 101, when it is being inserted into the cuvette 102, from coming into contact with an inner wall of the cuvette 102, which may cause a capillary effect that can lift up part of the testing reagent and lower the level thereof in the colorimetric section 2013 to an extent unsuitable for the intended colorimetric test. In other embodiments of the present invention, the holder section 2012 and the colorimetric section 2013 may both be hollow cylinders, wherein the slit 2014 is formed in a central area of the lid 2011 so that the tear glucose test strip 101 is prevented from coming into contact with the inner wall of the cuvette 102.

The colorimetric section 2013 contains a glucose oxidase endpoint assay reagent for an elution reaction. The glucose oxidase endpoint assay reagent includes a phosphate buffer, glucose oxidase, peroxidase and 3,3',5,5'-tetramethylbenzidine as a chromogen.

Specifically, use of the device may be as described below.

At first, in order to collect tears, the leading portion 1014 is grasped by tweezers to folde the leading portion 1014 by 90 degrees about the folding line 1021.

Subsequently, the lower eyelid of an eye is rolled outward with one hand, and the leading portion 1014 of the tear glucose test strip 101 is inserted into the lower conjunctival sac inside the lower eyelid with the other hand so that the holder portion 1015 hangs outside the lower eyelid. After the collection is completed, the leading portion 1014 of the tear glucose test strip 101 is pulled out. These operations are simple and can be performed by the user himself.

After that, the tear glucose test strip 101 is inserted through the slit 2014 into the cuvette 102 to allow an elution reaction with the glucose oxidase endpoint assay reagent contained in the colorimetric section 2013 of the cuvette 102.

5-10 Minutes later, the tear glucose test strip 101 is taken out and a chromogenic device measures a glucose level in the tears. As the tear glucose level is correlated to a blood sugar level of the user, the blood sugar level can be determined based on the tear glucose level.

Embodiment 2

Figure 4:
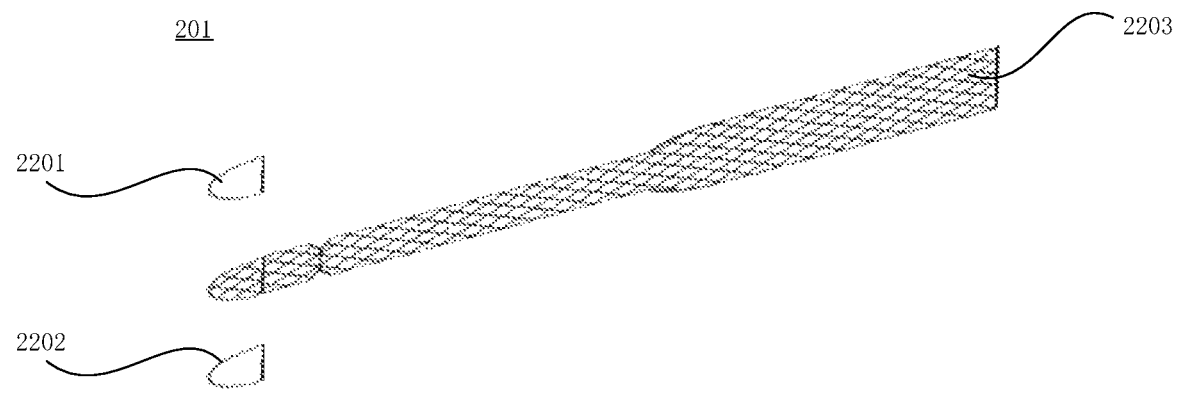
FIG. 4 is a structural schematic of a tear glucose test strip according to a second embodiment of the present invention.

In an embodiment of the present invention, there is also provided a tear glucose measuring device, which, as shown in FIG. 4, includes a tear glucose test strip 201 having a tear collection region made up of a stack of a first moisture-absorbent layer 2201, a second moisture-absorbent layer 2202 and a portion of a hydrophobic layer 2203. The hydrophobic layer 2203 is sandwiched between the first moisture-absorbent layer 2201 and the second moisture-absorbent layer 2202. The test strip also has a barrier region and a holder portion, each consisting of a portion of the hydrophobic layer 2203. In addition, the first moisture-absorbent layers 2201 and the second moisture-absorbent layer 2202 include, but not limited to, wood or cotton fibers. The hydrophobic layer 2203 includes, but not limited to, a polyethylene (PE) film. The other parts are the same as those in Embodiment 1, and a further description thereof is deemed unnecessary.

Figure 5:
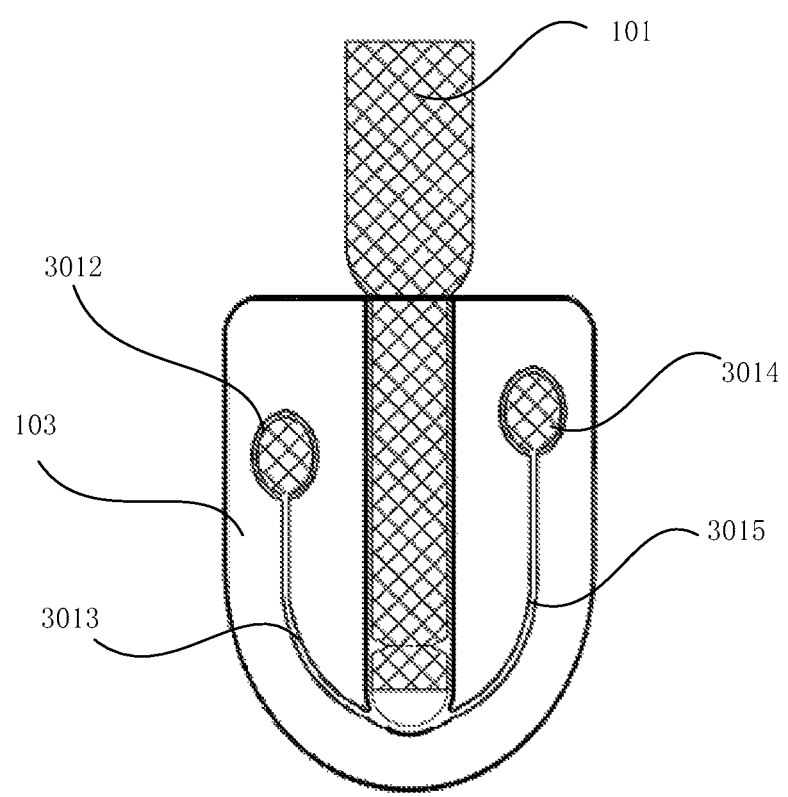
FIG. 5 is a structural schematic of a tear glucose measuring device according to the second embodiment of the present invention.
Figure 6:
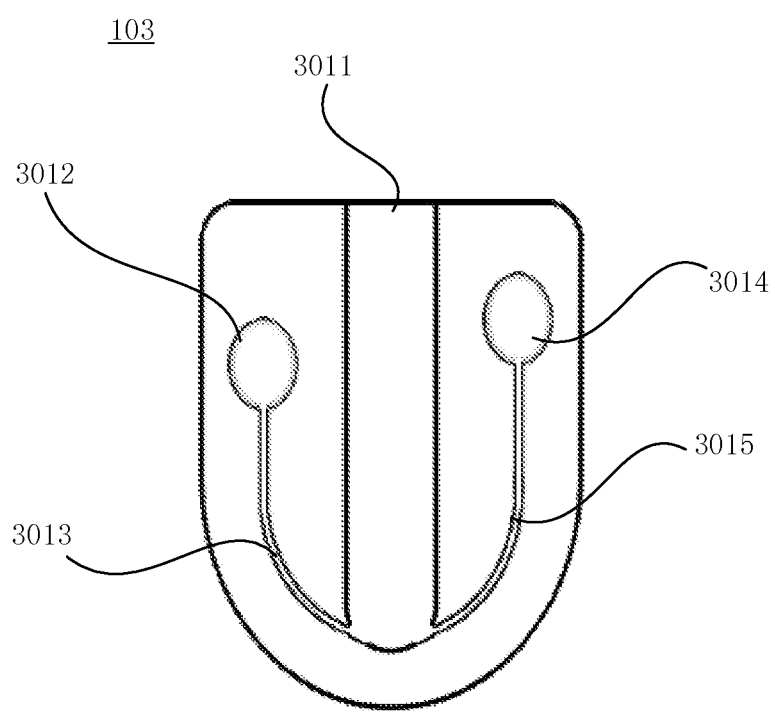
FIG. 6 is a structural schematic of a fluorescence plate according to the second embodiment of the present invention.

As shown in FIGS. 5 and 6, the tear glucose measuring device further includes a reaction device which is a fluorescence plate 103, the fluorescence plate 103 has a shape of horseshoe and includes a pocket 3011, a first reservoir 3012 and a second reservoir 3014, wherein the first reservoir 3012 is in communication with the bottom of the pocket 3011 via a first channel 3013 and the second reservoir 3014 is in communication with the bottom of the pocket 3011 via a second channel 3015. When the tear glucose test strip 101 is inserted into the pocket, the leading portion 1014 is located at the bottom of the pocket 3011.

Additionally, the tear glucose test strip 101 has a shoulder portion 1017 that has a width greater than that of the pocket 3011 so that when the tear glucose test strip 101 is inserted in the pocket 3011, the leading portion 1014 and first holder portion 1015 of the tear glucose test strip 101 are received within the pocket 3011 while the second holder portion 1016 of the tear glucose test strip 101 remaining out of the pocket 3011.

In this embodiment, the reagents for tear glucose testing include luminol (a luminescent chemical) as a chromogen, and the reagents include first and second reagents, the first reagent contains a phosphate buffer and glucose oxidase and the second reagent contains an alkaline salt buffer, peroxidase and luminol (a luminescent chemical).

The first reagent is disposed in the first reservoir 3012, and the second reagent in the second reservoir 3014. After tears are collected, the tear glucose test strip 101 is inserted into the pocket 3011 so that the leading portion 1014 of the tear glucose test strip 101 is located at the bottom of the pocket 3011. The first reservoir 3012 is then squeezed to cause the first reagent therein to flow into the pocket 3011 via the first channel 3013 to react with the tear collection region 1020 of the tear glucose test strip 101. 2-5 Minutes later, the second reservoir 3014 is squeezed to cause the second reagent therein to enter the pocket 3011 to further react with the tear collection region 1020 of the tear glucose test strip 101. The reaction results in the emission of fluorescence from the bottom of the pocket 3011. Strength of the fluorescence is proportional to the concentration of glucose in the collected tears, which is in turn well correlated to the blood sugar level of the diabetic patient. Therefore, the blood sugar level can be obtained from the tear glucose level measured by a fluorescence meter.

The other parts are the same as those in Embodiment 1, and a further description thereof is deemed unnecessary.

To sum up, with the tear glucose measuring devices according to the embodiment of the present invention, the user can collect tears by himself by folding the leading portion of the tear glucose test strip about the folding line and inserting the leading portion into the lower conjunctival sac inside the lower eyelid. As the tear collection region of the leading portion has a fixed area, it can collect a quantitative amount of tears. As such, tears can be sampled without needing to stimulate the lacrimal gland, and glucose in the collected tears will not be diluted and reflect the patient's true tear glucose level.

The preferred embodiments presented above are merely examples and are in no way meant to limit the present invention. Any changes such as equivalent alternatives or modifications made by those skilled in the art to the subject matter or features thereof disclosed herein without departing from the teachings of the present invention are considered to fall within the scope of the invention.

What is claimed is:

1. A tear glucose measuring device comprising: a tear collection strip and a reaction device, the tear collection strip configured for collecting tears which are then subjected to an elution reaction with a glucose assay reagent contained in the reaction device, the tear collection strip having a strip shape and comprising a leading portion and a holder portion,
    wherein the leading portion comprises: a tear collection region for collecting tears; and a barrier region for limiting an amount of tears collected by the tear collection region,
    wherein the tear collection region and the barrier region are demarcated by a boundary line, such that tears collected in the tear collection region cannot cross over the boundary line into the barrier region,
    wherein the reaction device is a cuvette comprising a holder section, a colorimetric section and a lid, the holder section in communication with the colorimetric section, the lid disposed on a top of the holder section and configured to seal the holder section and the colorimetric section, the lid defining a slit extending diagonally in the lid, wherein the leading portion of the tear collection strip is insertable through the slit into the cuvette to be dipped in the glucose assay reagent contained in the colorimetric section to enable the elution reaction.

2. The tear glucose measuring device according to claim 1, wherein the leading portion and the holder portion have a folding line formed therebetween, the leading portion being foldable about the folding line, and wherein on each side of the folding line there is formed a V-notch.

3. The tear glucose measuring device according to claim 1, wherein: the tear collection region comprises a first portion of a moisture-absorbent layer; the barrier region comprises a stack of a portion of a first hydrophobic layer, a second portion of the moisture-absorbent layer and a portion of a second hydrophobic layer, and the second portion of the moisture-absorbent layer is sandwiched between the portion of the first hydrophobic layer and the portion of the second hydrophobic layer.

4. The tear glucose measuring device according to claim 3, wherein: the holder portion comprises a stack of another portion of the first hydrophobic layer, a third portion of the moisture-absorbent layer and another portion of the second hydrophobic layer, and the third portion of the moisture-absorbent layer is sandwiched between the another portion of the first hydrophobic layer and the another portion of the second hydrophobic layer.

5. The tear glucose measuring device according to claim 1, wherein: the tear collection region comprises a first moisture-absorbent layer, a first portion of a hydrophobic layer and a second moisture-absorbent layer; the first portion of the hydrophobic layer is sandwiched between the first moisture-absorbent layer and the second moisture-absorbent layer; and the barrier region comprises a second portion of the hydrophobic layer.

6. The tear glucose measuring device according to claim 5, wherein the holder portion comprises a third portion of the hydrophobic layer.

7. The tear glucose measuring device according to claim 1, wherein the leading portion has a length of 4 mm to 6 mm.

8. The tear glucose measuring device according to claim 1, wherein the holder portion comprises a first holder portion and a second holder portion joined to each other, and wherein the first holder portion has a width smaller than a width of the second holder portion.

9. The tear glucose measuring device according to claim 8, wherein the first holder portion of the tear collection strip is insertable into the cuvette, the slit having a length smaller than the width of the second holder portion.

10. The tear glucose measuring device according to claim 9, wherein each of the holder section and the colorimetric section has a shape of a hollow column, and wherein the holder section has a size greater than a size of the colorimetric section.

11. The tear glucose measuring device according to claim 10, wherein each of the holder section and the colorimetric section has a shape of a hollow rectangular parallelepiped.

12. The tear glucose measuring device according to claim 9, wherein the glucose assay reagent comprises a phosphate buffer, glucose oxidase, peroxidase and 3,3',5,5'-tetramethylbenzidine as a chromogen.

* * * * *